United States Patent [19]

Tocker

[11] Patent Number: 4,722,838

[45] Date of Patent: Feb. 2, 1988

[54] SELF-MICROENCAPSULATING CONTROLLED RELEASE PESTICIDE COMPOSITIONS

[75] Inventor: Stan Tocker, Wilmington, Del.

[73] Assignee: E. I. Du Pont de Nemours and Company, Wilmington, Del.

[21] Appl. No.: 861,700

[22] Filed: May 9, 1986

[51] Int. Cl.[4] .................... A01N 25/10; A61K 31/78; B01J 13/02

[52] U.S. Cl. ................................ 424/81; 71/DIG. 1; 264/4.6; 424/406; 424/408; 424/455; 424/462; 424/497; 428/402.24; 514/941; 514/963

[58] Field of Search ................... 264/4.6; 428/402.24; 71/DIG. 1; 514/941, 963; 424/406, 408, 455, 462, 497, 81

[56] References Cited

U.S. PATENT DOCUMENTS

| 3,523,906 | 8/1970 | Vrancken et al. | 264/4.6 |
|---|---|---|---|
| 3,523,907 | 8/1970 | Vrancken et al. | 264/4.6 |
| 3,737,337 | 6/1973 | Schnoring et al. | 264/4.6 X |
| 3,894,149 | 7/1975 | Mast | 514/941 X |
| 4,080,191 | 3/1978 | Harvey | 71/DIG. 1 |
| 4,282,209 | 8/1981 | Tocker | 424/81 |
| 4,286,020 | 8/1981 | Himel et al. | 264/4.6 X |
| 4,324,781 | 4/1982 | Okamoto et al. | 514/941 X |

OTHER PUBLICATIONS

*Microcapsule Processing and Technologies*, A. Kondo (Marcel Denker, Inc., New York), chapter 8, pp. 70–94 (1979).

*Primary Examiner*—Richard D. Lovering

[57] ABSTRACT

This invention relates to a self-microencapsulating pesticidal composition consisting essentially of a solution of a polymeric barrier material in an organic solvent system, a dissolved or dispersed pesticidal agent and a surfactant.

17 Claims, No Drawings

SELF-MICROENCAPSULATING CONTROLLED RELEASE PESTICIDE COMPOSITIONS

BACKGROUND OF THE INVENTION

Controlled release pesticidal compositions offer several possible advantages over conventional compositions. First, they are usually more economical, as fewer pesticide applications to the crop are necessary. Controlled release compositions offer safety to the environment by preventing pesticide overuse and run-off or soil (translocation) leaching into unwanted neighboring areas such as water ways and wells. They can also offer safety to the crop in instances when large doses of conventional formulations are phytotoxic and provide safety to workers applying pesticides in the field by reducing the toxicity of the pesticide. Finally, controlled release compositions allow the effective use of pesticides which are too rapidly degraded, volatilized or leached away by rain in conventional formulations (i.e., conventional pesticides with very low residual activity).

The most common method of applying agricultural pesticides has involved addition to water as diluent and spraying. This generally requires that the dispersed particles be no greater in size in their largest dimension than 50 microns, preferable under 20 microns. Many processes for preparing controlled release products reported in the prior art would not provide such small particles suitable for spraying. These processes are summarized in *Microcapsule Processing and Technology,* A, Kondo (Marcel Denker, Inc., New York).

Major difficulties have been encountered in the production, storage and use of controlled release formulations depending on the active material employed. For example, it is especially difficult to encapsulate active materials that are solid and have low thermal and hydrolytic stability, such as carbamate insecticides and sulfonylurea herbicides. Essentially all of the prior art methods required have one or more disadvantages in that they (1) require heating, (2) require use of water or aqueous acid or base that can decompose hydrolytically unstable materials during the process or storage, (3) require a tedious step such as slow cooling or slow addition of a component, e.g., polymer precipitation agent, (4) require chemically active ingredients such as polyfunctional isocyanates or acid chlorides to form polymers, increasing the possibility of chemical attack on the active material, or contamination of the formulation with by-products of the polymerization reaction, and (5) do not produce particles small enough (under 50 microns in their longest dimension) to be conveniently sprayed without clogging spray nozzles.

Microencapsulation techniques have been reported that provide sprayable aqueous suspensions having slow release characteristics. A widely used process for microencapsulation involves interfacial polymerization, i.e., dispersion of a solution of active material in water by intensive mixing and then production of a polymeric shell at the interface of suspended microdroplets of active material and the continuous water phase. Interfacial polymerization requires the use of polyfunctional, chemically active monomers such as diacid chlorides of polyisocyanates in admixture with the active and a catalyst or complimentary monomer dissolved in the water phase. After the formation of the microcapsules, the aqueous microcapsule suspension can be treated with stabilizers and stored and later distributed as an aqueous suspension. A commercial example of this is Penn-Cap® M, a microencapsulated methyl parathion (Pennwalt Corporation). While this type of aqueous formulation is suitable for relatively stable liquids such as methyl parathion, it is not useful with bioactive materials that are either relatively insoluble in the organic monomers or show hydrolytic instability upon prolonged storage in the presence of water. Filtration of such small microcapsules and drying immediately after manufacture in an attempt to isolate them from the water for long-term storage is slow and adds two additional steps to the process.

The prior art also involves physical processes for preparing slow-release particles containing polymer barriers. The common feature of these is the use of preformed polymers.

U.S. Pat. No. 3,523,906 discloses the preparation of polymer microcapsules for agricultural or pharmaceutical use by dispersing an organic polymer solution containing the dissolved or dispersed active agent in water and precipitating the polymer by evaporation or organic solvent. This process employs a water-insoluble organic solvent for the polymer and generally produces particles over 50 microns in size that cannot be sprayed by conventional methods and solvent removal is a time consuming step that involves solvent recovery and recycling.

U.S. Pat. No. 3,523,907 discloses the preparation of polymer microcapsules by dispersing an organic polymer solution in water and adding an additional solvent that while miscible with water and the organic solvent, causes the precipitation of the polymer. Addition of the organic solvent to produce precipitation is a tedious and slow step requiring much care to avoid agglomeration of the particles.

U.S. Pat. No. 4,282,209 discloses the preparation of irregularly shaped controlled release particles (not microcapsules) by mixing an organic (acetone) solution of an active agent and a polymer with water (precipitating solvent) under high shear conditions. This process requires relatively large quantities of organic solvents that must be recycled. Also, physical abuse of the preformed particles during intensive mixing could produce cracks in the particles and consequently, too rapid a release rate.

SUMMARY OF THE INVENTION

This invention relates to a self-microencapsulating pesticidal composition consisting essentially of a solution of a polymeric barrier material in a specific type of organic solvent system, a dissolved or suspended pesticidal agent, and surfactant system. Addition of this composition to water with mild agitation results in the essentially instantaneous formation of an aqueous suspension of liquid or solid spherical microcapsules under 50 microns in size which provide upon application by spraying to the locus to be protected unusually low controlled release rates of the active pesticidal agent. Microencapsulated pesticidal composition and their preparation are described in *Microcapsules and Microcapsulation Techniques,* Noyes Data Corporation, Park, Ridge, N.J. (1976). Encapsulation means pesticide mixtures with the polymeric barrier or coatings of the polymeric barrier on the pesticide or both. What is meant by essentially instantaneous is mixing for less than 10 seconds to form the suspension or microcapsules.

A formulation of the organic solvent system, polymer barrier, and surfactant components must be selected so that when the formulation is added to water, the formation of small dispersed droplets precedes dissolution of solvent in the water. The composition in the form of a dispersion or solution must have a viscosity of less than 1500 cp at 20° C. as measured by Brookfield Viscometer. The Brookfield Viscometer is a device for measuring viscosity by sensing the torque required to rotate a spindle at constant speed while immersed in a sample fluid. Such instruments are manufactured by Brookfield Engineering Laboratories, Inc., Stoughton, Mass. If the viscosity is too high, the dispersion rate in water would be too slow which leads to the formation of large unsprayable aggregates. The composition must be essentially instantaneously dispersible in water with mild agitation. Preferably, the composition must be dispersed in water with mild agitation in less than one second.

The organic solvent system is made up of at least one organic solvent having a hydrogen bonding index such that the affinity of the solvent for water is sufficiently low to permit the solution of the organic solvent and barrier material to form small immiscible droplets of the solution in the water before substantial dissolution of the solvent in the water occurs. The solvent system includes solvents with a hydrogen bonding index of less than 5.7. However when more than one solvent is used a solvent with a hydrogen bonding index of 5.7 or more may be used provided it constitutes no more than 50% by weight of the total solvent. A further requirement when more than one solvent is used is that no more than 50% by weight of the total weight of solvent is composed of a water-insoluble solvent. There are many solvents that may be used that have the necessary hydrogen bonding index and these are known in the art.

The organic solvent system may consist of a single solvent or a mixture of solvents. Use of additional solvent or solvents may be required to (1) ensure complete dissolution of a given active or polymer, (2) reduce the rate of extraction of the solvent into the water and the rate of release of the active from the capsules and (3) reduce the viscosity of the composition so as to improve the rate of dispersion. The use of one organic solvent less soluble in water than the other organic solvent(s) in a mixture of organic solvents permit a reduction in the rate of extraction of the solvent from the polymeric barrier material into the water. Examples of operable water-soluble solvents include ethyl acetate, cyclohexanone, isopropylacetate, tetrahydrofuran, and methyl ethyl ketone. The most preferred water-soluble solvents are ethyl acetate and cyclohexanone. Examples of water-insoluble cosolvents are toluene and xylene.

When a suspension of the active pesticide in the polymer solution was used, containing no water-soluble solvent, polymer-coated particles were obtained, the shapes of which roughly conformed to that of the undissolved particles. If a water insoluble cosolvent is included in such a suspension formulation, round liquid microspheres were obtained, ranging in viscosity from a liquid to semi-solid, depending on the amount of water-insoluble solvent used and molecular weight of the polymer.

On the other hand, where the active material is dissolved in the polymer solution, solid microspheres were obtained upon use of a water-soluble cosolvent. If a water-insoluble solvent or cosolvent is used in the solution formulation, round microspheres were obtained ranging in viscosity from a liquid to a semi-solid, again dependent on composition.

The polymer barrier material may be a polymer or a mixture of polymers that are completely soluble in the organic solvent systems and also provide good resistance to permeation by water. Polymers that are preferred have a water absorption rate of 0.4 or less in 24 hours on a ⅛" thick specimen (ASTM test method D570) and which are soluble in the solvent system of this invention. Such barrier materials provide a slow release of the pesticidal agent from the resultant microcapsule. Preferably., this release is at a rate that provides for less than 50% of the pesticidal agent to dissolve in 24 hours at 20° C. in sufficient water to solubilize all the pesticidal agent. Representative examples of polymeric barrier materials include polymethylmethacrylate, polyvinyl chloride, polystyrene, vinyl chloride/vinylidene chloride copolymers, polysulfones and polyethylmethacrylate.

The surfactant or surfactant mixture is selected so as to provide rapid dispersion of the pesticidal composition in water before the solvent is dissolved. Surfactants that provide such a rapid dispersion in water can be characterized by their HLB number. (The hydrophilic-lipophilic balance of the surfactant. This value and its method of determination are discussed in *Pesticide Formulations*, W. V. Valkenburg, Marcel Denker, Inc., New York, p. 76–90.) Preferably the surfactant or surfactant mixture has an HLB of 10–17. Representative examples of such surfactants are polyoxyethylene sorbitan monoalkyl esters such as Tween ® 20, 60 and 80, made by ICI Americas, Inc., Wilmington, Del. and other polyoxyethylene nonionic surfactants. The most preferred surfactant, Tween ® 80, is a polyoxyethylene sorbitan monooleate.

The composition of the organic solvent system, polymer barrier, active pesticidal agent, and surfactant are selected to afford a dispersion or solution having a viscosity of less than 1500 cp at 20° C. and resulting microcapsules that release the active pesticidal agent at a rate less than 50% in 24 hours at 20° C. in an amount of water of sufficient excess to dissolve all of the active agent.

Thus the invention is a self-microencapsulating pesticidal composition consisting essentially of a solution of a polymeric barrier material dissolved in an organic solvent system, a dissolved or dispersed pesticidal agent and at least one surfactant, said composition having a Brookfield viscosity of less than 1500 cm at 20° C. wherein (1) the organic solvent system comprises at least one organic solvent having a hydrogen bonding index of less than 5.7 and a rate of dissolution in water that permits the solution of the organic solvent and barrier material to form small immiscible droplets of the solution in the water before substantial dissolution of the solvent in the water occurs, (2) the polymeric barrier is completely soluble in the organic solvent system and (3) the surfactant having a HLB that will permit the surfactant to provide rapid dispersion of the composition in water before the solvent dissolves. The above composition when added to water will essentially instantaneously form with mild agitation particles of less than 50 microns.

It is preferred that the composition of the invention be dispersible in water with mild stirring in less than one second.

The composition of the invention can provide a microencapsulated pesticidal agent with unusually low rates of release of the pesticidal agent by simple addition to mildly agitated water. In some cases, it has been as low as zero percent released in 24 hours in excess water at room temperature, determined by ultraviolet analysis. In other cases, the release rate can be as high as 90% in 24 hours in excess water at room temperature.

The compositions of the invention are used by preparing an aqueous dispersion of the compositions by a simple mixing process involving mixing the organic solvent system, dissolved polymeric barrier materials, pesticidal agent, surfactant with the required amount of spray water to yield dispersions of liquid or solid microparticles ready for application by spraying.

Preparation of the composition of the invention does not require specialized equipment, elevated temperatures, reactive chemicals, multiple processing steps or any need to isolate the microcapsules by filtration prior to suspension as with other methods. This invention can provide extremely economical, controlled release, sprayable compositions because the user and not a manufacturing facility will carry out the preparation by merely following the customary process of adding an agrichemical to spray water and adding the composition of the invention to spray water.

The extraction of the active pesticidal agent from the polymeric barrier material is believed to be controlled by the permeability of the barrier material to water.

The preparation of the compositions of the present invention involve simply dissolving the polymer in the solvent and then adding the surfactant followed by the optional addition of other cosolvents, if necessary. Optionally, the materials can be chosen so that the active material is completely dissolved, partially dissolved or completely suspended. The hardness of the microcapsules can be adjusted by the amount of water-insoluble solvent used. Depending on the polymeric barrier selected, its molecular weight and the amount of water-insoluble solvent used, physical state of the microcapsules formed can range from liquid to hard, solid microspheres. Generally, use of relatively low molecular weight polymer and increasing amounts of water insoluble solvent will favor the formulation of liquid microcapulets.

In general, all the components work together to permit control over dispersibility, microsphere size and release rate.

The table below illustrates composition variations for adjusting the properties of the microcapsule suspension after the compositions of the present invention are added to water.

The compositions of the invention may vary to achieve optimum microsphere size and release rate of the pesticidal agent. Specifically, the average size of the microcapsules can be reduced by adding more solvent for the polymer, reducing the viscosity, or by adding more surfactant or by using low molecular weight polymers. The release rate of the microcapsules can be reduced by including a water-insoluble solvent, by using higher molecular weight polymer, by increasing the weight ratio of polymer:active pesticide or by selecting a polymer that is more water impermeable.

The compositions of the present invention can contain one or more polymeric barriers for obtaining desired properties. For example, the dispersibility and release rate of polymethyl methacrylate microcapsules can be increased by including increasing amounts of highly polar polymers such as cellulose acetate. Dispersibility can often be improved by including a mixture of surfactants instead of a single material.

The particle sizes were determined by microscopy. The release rates in excess water were determined by taking aliquots periodically from the aqueous suspension of microcapsules containing 0.02 g of active, diluting them to 1.0 liter with water, aging the resultant suspension 24 hours, filtration of about 10 mL of the solution and determining the concentration active in the water phase by ultraviolet analysis.

Illustrated below are examples of structures used in self-microencapsulating formulations.

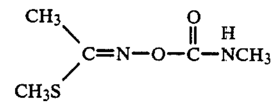

(I)

methomyl 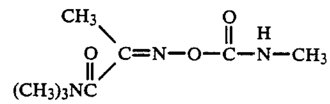 (II)

oxamyl 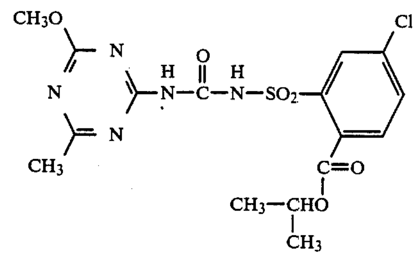 (III)

sulfonylurea DPX M5268

In Examples 1-5 of the invention that follow the dispersions occurred essentially instantaneously.

COMPARATIVE EXAMPLE A

A solution was made of 4.0 g technical methomyl (Du Pont Co.), structure I, 8.0 g 10% Elvacite ® 2008 polymethyl methacrylate (Du Pont Co.) in acetone, which has an HB index of 5.7, 1.0 g xylene and 1.0 g Tween ® 80 (ICI Americas, Inc.). The resultant solution was added to 800 mL of gently stirred water, resulting in the formulation of unsprayable lumps of polymer.

EXAMPLE 1

The composition of Example A was prepared in which acetone was replaced by cyclohexanone. When this formulation containing 28.6% methomyl was added to gently stirred water, a suspension of microspheres ranging in size from under 1.0 micron to 20 microns was formed. The release rate of these solid microspheres was 55% in 24 hours (excess water).

EXAMPLE 2

Example 1 was repeated except for the use of oxamyl (Du Pont Co.) as the active material, structure II, prepared by stripping solvent from commercial Vydate ® L (Du Pont Co.). This solution gave a microcapsule suspension in water containing microspheres averaging about 6.0 microns in size. The release rate in water in 24 hours was 65%.

EXAMPLE 3

A mixture of 0.5 g of finely ground sulfonylurea of structure III (DPX-M5268), 11.0 g of 2% Elvacite® 2010 dissolved in ethyl acetate and 2.0 g of Tween® 20 surfactant was added to 800 ml of water to produce a suspension of hard, irregular particles averaging about 10 microns in size. The release rate of the coated particles was determined to be 18% in excess water in 24 hours.

EXAMPLE 4

Example 3 was repeated except for the use of 11 g of 2% solution of a 1:1 weight ratio of Elvacite® 2010 and cellulose acetate as the polymer solution. The release rate was 31% in 24 hours.

EXAMPLE 5

A suspension was made of 1.0 g finely ground sulfonylurea (structure III), 11.0 g of 20% Elvacite® 2010 in a 1:1 xylene:cyclohexanone solution and 1.0 g of Tween® 80. When this was added to water, viscous liquid microcapsules averaging about 3 microns in size were obtained which showed a release rate of 9% in 24 hours in excess water.

What is claimed is:

1. A self-microencapsulating pesticidal composition which when added to water with mild stirring will form particles of the pesticide encapsulated with a polymer, said composition consisting essentially of a solution of a polymeric barrier material dissolved in an organic solvent system, a dissolved or dispersed pesticidal agent and at least one surfactant, said composition having a Brookfield viscosity of less than 1500 cp at 20° C. wherein (1) the organic solvent system comprises one or more solvents with at least one organic solvent having a hydrogen bonding index of less than 5.7 and a rate of dissolution in water that permits the solution of the organic solvent and barrier material to form small immiscible droplets of the solution in the water before substantial dissolution of the solvent in the water occurs, (2) the polymeric barrier is completely soluble in the organic solvent system and provides good resistance to permeation by water and (3) at least one surfactant having a HLB that will permit the surfactant to provide rapid dispersion of the composition in water.

2. The composition of claim 1 which when dispersed in water with mild stirring will form less than 50 micron particles of the pesticide encapsulated with the polymeric barrier in less than one second.

3. The composition of claim 2 wherein the organic solvent system comprises one organic solvent.

4. The composition of claim 2 wherein the barrier polymer is polymethylmethacrylate.

5. The composition of claim 2 wherein the surfactant is polyoxyethylene sorbitan monooleate.

6. The composition of claim 1 wherein the organic solvent system comprises one organic solvent.

7. The composition of claim 6 where the organic solvent is completely soluble in water.

8. The composition of claim 6 wherein the surfactant or mixture of surfactants has an HLB of 10–17.

9. The composition of claim 6 wherein the organic solvent is ethyl acetate or cyclohexanone.

10. The composition of claim 6 wherein the barrier polymer is polymethylmethacrylate.

11. The composition of claim 6 wherein the surfactant is polyoxyethylene sorbitan monooleate.

12. The composition of claim 1 wherein the organic solvent system comprises two solvents.

13. The composition of claim 12 wherein one solvent is insoluble in water and constitutes no more than 50% by weight of the total solvent and one solvent has a hydrogen bonding index of less than 5.7.

14. The composition of claim 13 wherein the surfactant is a polyoxyethylene nonionic derivative or a mixture thereof.

15. The composition of claim 13 wherein the surfactant or mixture of surfactants has an HLB of 10–17.

16. The composition of claim 13 wherein the barrier polymer is polymethylmethacrylate.

17. The composition of claim 13 wherein the surfactant is a polyoxyethylene sorbitan monooleate.

* * * * *